(12) United States Patent
Tjoeng

(10) Patent No.: US 7,094,872 B2
(45) Date of Patent: Aug. 22, 2006

(54) ACTIVATED POLYETHYLENE GLYCOL ESTERS

(75) Inventor: Foe S. Tjoeng, Ballwin, MO (US)

(73) Assignee: Pharmacia Corporation, Chesterfield, MO (US)

( * ) Notice: Subject to any disclaimer, the term of this patent is extended or adjusted under 35 U.S.C. 154(b) by 138 days.

(21) Appl. No.: 10/782,268

(22) Filed: Feb. 19, 2004

(65) Prior Publication Data

US 2004/0162388 A1    Aug. 19, 2004

Related U.S. Application Data

(60) Provisional application No. 60/448,354, filed on Feb. 19, 2003.

(51) Int. Cl.
*C07D 207/404* (2006.01)
*C07D 249/18* (2006.01)
*C07K 1/113* (2006.01)

(52) U.S. Cl. ............... 530/345; 530/409; 548/259; 548/520; 548/542

(58) Field of Classification Search ............. None
See application file for complete search history.

(56) References Cited

U.S. PATENT DOCUMENTS

| | | | |
|---|---|---|---|
| 4,658,021 A | 4/1987 | Goeddel et al. | 530/399 |
| 5,122,614 A | 6/1992 | Zalipsky | 548/520 |
| 5,281,698 A | 1/1994 | Nitecki | 530/351 |
| 5,382,657 A | 1/1995 | Karasiewicz et al. | 530/351 |
| 5,633,352 A | 5/1997 | Dalbøet al. | 530/399 |
| 5,650,234 A | 7/1997 | Dolence et al. | 428/447 |
| 5,932,462 A | 8/1999 | Harris et al. | 435/188 |
| 6,180,095 B1 * | 1/2001 | Greenwald et al. | 424/85.1 |
| 2002/0151682 A1 * | 10/2002 | Athwal et al. | 530/350 |

FOREIGN PATENT DOCUMENTS

EP    0 512 844 A    8/1992

OTHER PUBLICATIONS

Clark, R., et. al., Journal of Biological Chemistry, *Long-Acting Growth Hormones Produced by Conjugation with Polyethylene Glycol*, 36, 21969-21977, 1996.
Takeda, K., et. al., Tetrahedron Letters, *Convenient Methods for Syntheses of Active Carbamates, Ureas and Nitrosoureas Using N,N-disuccinimido Carbonate (DSC)*[1], 24, 4569-4572, 1983.
Takeda, K., Tetrahedron Letters, *A Convenient Synthesis of Peptide Using Oxallates*, 24, 4451-4454, 1983.
Takeda, K., J. Org. Chem., *1,1'-Bis[6-(trifluoromethyl)benzotriazolyl] Oxalate (BTBO):A New Reactive Coupling Reagent for the Synthesis of Dipeptides, Esters, and Thio Esters*, 50, 273-275, 1985.
Ghosh, A. K., Tetrahedron Letters, *N,N'-Disuccinimidyl Carbonate: A Useful Reagent for Alkoxycarbonylation of Amines*, 33, 2781-2784, 1992.

* cited by examiner

Primary Examiner—Jeffrey Edwin Russel

(57) ABSTRACT

The present invention relates to the preparation of polyethylene glycol carbonate active esters useful for the PEGylation of biological active and pharmaceutically useful peptides and proteins. The invention involves the use of activated carbonate and oxalate esters in the formation of polyethylene glycol mixed carbonate active esters that then react with a linker or directly with a target peptide or protein.

19 Claims, No Drawings

US 7,094,872 B2

ACTIVATED POLYETHYLENE GLYCOL ESTERS

The present application claims priority under Title 35, United States Code, §119 to U.S. Provisional application Ser. No. 60/448,354, filed Feb. 19, 2003, which is incorporated by reference in its entirety as if written herein.

FIELD OF THE INVENTION

The present invention relates to the preparation of polyethylene glycol carbonate active esters useful for the PEGylation of biological active and pharmaceutically useful peptides and proteins. The invention involves the use of activated carbonate and oxalate esters in the formation of polyethylene glycol mixed carbonate active esters that in turn react with a linker or directly with a target peptide or protein.

BACKGROUND OF THE INVENTION

A number of peptides and proteins have been developed as useful drugs largely by genetic engineering technique. However, their therapeutic potential is often severely limited due to their intrinsic properties as peptides or proteins. These molecules are readily metabolized by proteases and rapidly excreted by renal filtration. Furthermore, they may induce immunological reactions even if their sequences are similar to human proteins. It is therefore desirable to develop biologically more stable and long acting peptide- or protein-based drugs by chemical modification.

Polyethylene glycol (PEG) is a hydrophilic, biocompatible and non-toxic water-soluble polymer of general formula H—$(OCH_2CH_2)_n$—OH, wherein n>4. Its molecular weight varies from 300 to 40,000 Daltons.

It has been demonstrated that the conjugation of PEG to proteins and/or peptides significantly increases their duration of biological activity. PEG provides a more stable conformation and increases the size of the molecule, thus reducing its metabolic degradation and renal clearance. Furthermore, PEGylation may reduce the immunogenecity and improve the solubility of the peptide or the protein.

Various PEG-protein conjugates were found to be protected from proteolysis and/or to have a reduced immunogenicity [Monfardini, et al., Biocon. Chem., 6, 62–69 (1995); and Yamsuki et al., Agric. Biol. Chem., 52, 2185–2196 (1988)]

PEG conjugation is an already established methodology for peptide and protein modification pioneered by the work of Davis and Abuchowski [Abuchowski, A. et al, J. Biol. Chem., 252, 3571 (1977) and J. Biol. Chem., 252, 3582 (1977)]. PEG conjugation to peptides or proteins generally involved the activation of PEG and coupling of the activated PEG-intermediates directly to target proteins/peptides or to a linker, which is subsequently activated and coupled to target proteins/peptides. One of the key issues with the conjugation is the chemistry used to activate PEG and PEG-linker, which in turn will determine the coupling efficiency and specificity of the activated PEG or PEG-linker to its targets.

For example, the trichlorotriazine—activated PEG, which was found to be toxic and non-specific, was later on replaced by various activated PEG that could react specifically to amino group of the target peptides or proteins [Bencham C. O. et al., Anal. Biochem., 131, 25 (1983); Veronese, F. M. et al., Appl. Biochem., 11, 141 (1985).; Zalipsky, S. et al., Polymeric Drugs and Drug Delivery Systems, adrs 9–110 ACS Symposium Series 469 (1999); Zalipsky, S. et al., Europ. Polym. J., 19, 1177–1183 (1983); Delgado, C. et al., Biotechnology and Applied Biochemistry, 12, 119–128 (1990)], to sulfhydryl group [Sartore, L., et al., Appl. Biochem. Biotechnol., 27, 45 (1991); and Morpurgo et al., Biocon. Chem., 7, 363–368 (1996)] or to guanidine residues [Pande, C. S. et al., Proc.Nat.Acad.Sci., 77, 895–899 (1980)]. Another technical difficulty in protein PEGylation arises from the fact that a protein or a peptide often contains not only different functional groups such as amino, guanidine, hydroxyl or sulfhydryl, but it also has more than one of them. As a result, the product contains a mixture of conjugates with different PEG-protein stochiometries. The conjugation of PEG to growth hormone (GH) represents a typical example of such problem [Clark, R. et al., J. Biol. Chem., 36, 21969–21977 (1996)]. It was demonstrated that Lys residues of GH were PEGylated at random positions. Site-specific PEGylation of a protein remains a chemical challenge.

To increase the coupling specificity of the PEG to a protein or peptide, without significantly reducing its coupling efficiency, the carbonate esters of PEG have been frequently used to form the PEG-peptide or PEG-protein conjugates. N,N'-disuccinimidylcarbonate (DSC) has been used in the reaction with PEG to form active mixed PEG-succinimidyl carbonate that was subsequently reacted with a nucleophilic group of a linker or an amino group of a target protein/peptide (U.S. Pat. Nos. 5,281,698 and 5,932,462). In a similar type of reaction, 1,1'-(dibenzotriazolyl)carbonate and di-(2-pyridyl)carbonate have been reacted with PEG to form PEG-benzotriazolyl and PEG-pyridyl mixed carbonate (U.S. Pat. No. 5,382,657), respectively.

However, the carbonate esters are not easily prepared. In general, to achieve good yield, phosgene is often used in their preparation. This reagent can be difficult to handle and dangerous in the large-scale synthesis.. Thus, the use of other but similar active esters, such as N,N'-disuccinimidyl oxalate and 1,1'-bis[6-(trifluoromethy)benzo-triazolyl] oxalate, which are prepared from oxalyl chloride, may be superior and safer in the preparation of PEG mixed carbonate active esters. Furthermore, the oxalate active esters can be more economically prepared than the carbonate active ester.

SUMMARY OF THE INVENTION

The present invention describes a method for the preparation of an activated polymer ester for attachment to biologically active nucleophiles, with or without a linker. More specifically, the present invention relates to a method for producing an activated ester of polyethylene glycol (PEG), comprising reacting a polyethylene glycol (PEG), which has at least one free hydroxyl group, with an oxalate ester under the appropriate reaction conditions to form a PEG active ester. The oxalate esters used in the present invention are N,N'-disuccinimidyl oxalate and 1,1'-bis[6-(trifluoromethy)benzotriazolyl] oxalate.

It has been demonstrated that the resulting PEG active ester will react under appropriate conditions in a specific manner with the biologically active nucleophiles (U.S. Pat. Nos. 5,281,698, 5,650,234, and 5,932,462). More specifically, with the amino group of the peptides or proteins to form a stable urethane linkage between the polymer and the peptide or protein.

Another embodiment of the present invention is the PEG mixed carbonate active esters prepared by the process described in the present invention. Preferably, the PEG mixed carbonate esters include, for example, PEG-succinimidyl and PEG-6-(trifluoromethy)benzotriazolyl mixed carbonate esters.

Another embodiment of the present invention is the PEG-biologically active nucleophile conjugates, with or without linker, prepared by the methods described in the present invention. Preferably, the PEG-biologically active nucleophile conjugates include PEG-peptide and PEG-protein conjugates, with or without linker.

In another embodiment of the present invention wherein the biological active nucleophile is preferably a peptide or a protein. Preferred proteins encompassed in the present invention are human GH as disclosed in U.S. Pat. Nos. 4,658,021 and 5,633,352 and antibodies or their fragments such as antibody against $TNF_\alpha$, antibody against human GH receptor, antibody against C-Met, and antibody against IGF-1 receptor.

A preferred $TNF_\alpha$ antibody is a CDR-grafted, hTNF40-based modified Fab as previously disclosed in US patent application 2002/151682 A1.

In another embodiment of the present invention wherein the PEG active ester is first reacted with a linker and then, coupled to a biologically active nucleophile. More specifically, for example, the PEG active ester is reacted with an excess of 1,3-diaminopropane. The resulting (PEG)-O—C(O)—NH—$(CH_2)_3$—$NH_2$ conjugate is then coupled with N-carboxymethylmaleimide. This PEG-linker conjugate is further coupled with a biological active nucleophile, more specifically with the Cys residue of an antibody or antibody fragment, for example, with an anti-$TNF_\alpha$ modified $F_{ab}$ to form CDP 870. CDP 870, a PEGylated, anti $TNF_\alpha$, modified $F_{ab}$, is an effective antibody against rheumatoid arthritis.

A further embodiment is a method of treating a patient in need thereof is by administering a therapeutically effective amount of PEG-peptide or PEG-protein conjugate prepared by the process disclosed in the present invention.

The oxalate esters of the present invention are either commercially available or can be easily and economically prepared. Their preparation involves the use of oxalyl chloride instead of phosgene. Oxalyl chloride is easier and safer to handle than phosgene in the large-scale synthesis. Due to the lower cost of the starting materials and higher overall yields, the oxalate esters can be more economical to prepare than the corresponding carbonate esters. In addition, the oxalate esters are generally more stable than the carbonate esters and can be kept at room temperature over a long period of time. Furthermore, as discussed above, the PEG active esters have the advantage of increased specificity.

Thus, these reagents should provide additional improvements for the preparation of the increasingly importance PEGylated peptides and proteins that are useful for treatment of various diseases. This PEGylation process can improve the solubility, reduce the immunogenecity, and increase the metabolic stability of peptides or proteins.

DETAILED DESCRIPTION OF THE INVENTION

Chemistry

Similar to carbonate esters [Takeda, K. et al., Tetrahed. Lett., 24, 4569–4572 (1983)], oxalate esters such as N, N'-disuccinimidyl oxalate (I, DSO), and 1,1'-bis[6-(trifluoromethy)benzotriazolyl]-oxalate (II) have been successfully used in the preparation of carbamate derivatives and in the peptide synthesis [Takeda, K. et al., Tetrahed lett., 24, 4451–4454 (1983); J. Org. Chem., 50, 273–275 (1985);

Ghosh, A. K., Tetrahed. Lett., 33, 2781–2784 (1992]. However, the reactions of these reagents with PEG to form mixed carbonate active esters have not been reported.

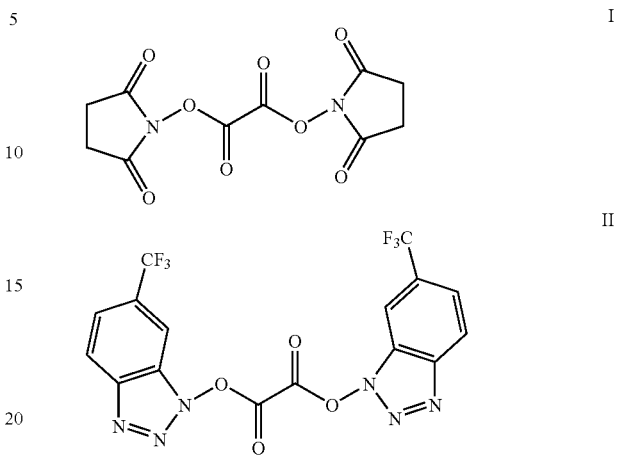

The present invention relates to the use of these reagents in the preparation of activated PEG carbonate (III and IV) esters that are useful in the synthesis of PEGylated biological active nucleophiles, more specifically PEGylated peptides or proteins. This process can improve the solubility, reduce the immunogenecity, and increase the metabolic stability of peptides or proteins.

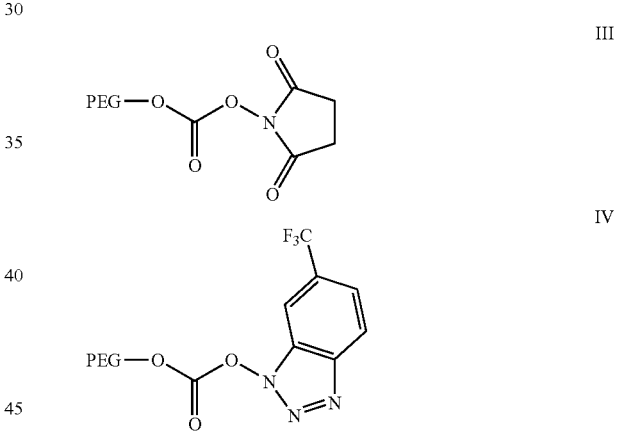

In one embodiment of the present invention, the method comprises of a reaction of a PEG with N,N'-disuccinimidyl oxalate (I) in the presence of a base catalyst to form compound III, as illustrated in SCHEME I. The base catalyst that is suitable for use in this and all following reactions with the oxalate or carbonate active esters includes organic bases such as pyridine and N, N'-4-dimethylaminopyridine (DMAP).

SCHEME I

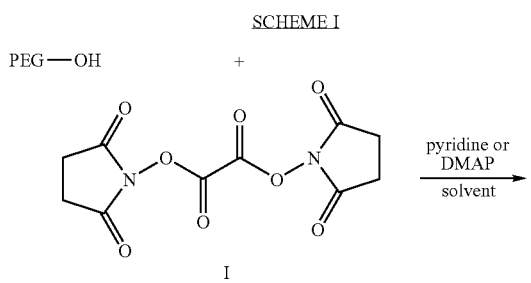

-continued

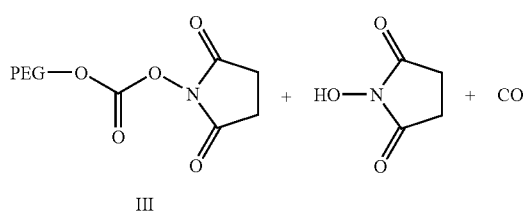

III

N,N'-disuccinimidyl oxalate (I) can be prepared according to the procedure described by K. Takeda [Tetrahed. Lett., 24, 4451–4454 (1983)] from N-hydroxysuccinimide and oxalyl chloride in the presence of pyridine as shown in SCHEME II.

SCHEME II

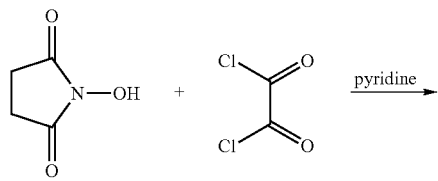

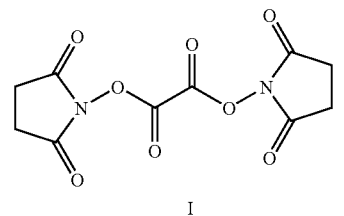

I

It should be understood that even though polyethylene glycol (PEG) is mentioned, all other recited forms of PEG in the present invention can also be used. In general, PEG has one free hydroxyl groups at each end of the polymer molecule. Preferably, the PEG used in the present invention, has at least one free terminal hydroxyl group. It is this hydroxyl group which is activated to react with a free amino group of a protein or a linker. In this case, PEG is reacted with N,N'-disuccinimidyl oxalate in the presence of N,N'-dimethylaminopyridine or pyridine to form a relatively stable and active N-succinimidyl carbonate ester. This PEG active ester will then react specifically with the amino group of a peptide or a protein to form a stable urethane linkage.

Alternatively, the PEG active ester will react with the amino group of a linker such as ω,ω-aminoalkane or aminoalkanoic acids. Subsequently, the PEG-linker conjugate is activated or reacted with another activated moiety, and then coupled with the amino group of a peptide or a protein.

In another embodiment of the present invention, a PEG is reacted with 1,1'-bis[6-(trifluoromethy)benzotriazolyl] oxalate (II) in the presence of a base to form compound IV as illustrated in SCHEME III

SCHEME III

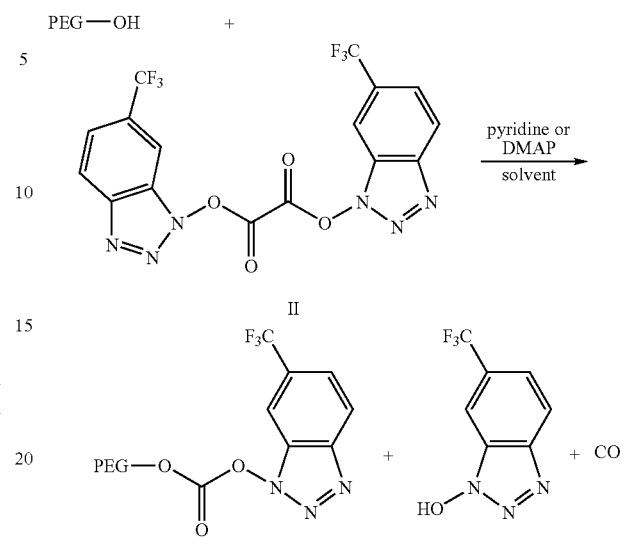

Similar to the reaction of PEG with N,N'-disuccinimidyl oxalate (I), the reaction is catalyzed by an organic base such as pyridine or DMAP. The starting material, 1,1'-bis[6-(trifluoromethy)benzotriazolyl] oxalate (II) can be prepared by a two-steps procedure described by K. Takeda [J. Org. Chem., 50, 273–275 (1985)] from 4-chloro-3-nitro-α,α,α-trifluorotoluene as shown in Scheme IV.

SCHEME IV

Subsequently, these PEG active ester intermediates are coupled covalently via a urethane bond to the amino group of the target peptide or protein. Alternatively, these intermediates are first coupled to one or more linkers such as ω,ω-aminoalkane, N-carboxyalkylmaleimide, or aminoalkanoic acids and then, with or without further activation, to a amino or a thiol group of a peptide or a protein as illustrated in the following Schemes V, VI and VII.

SCHEME V
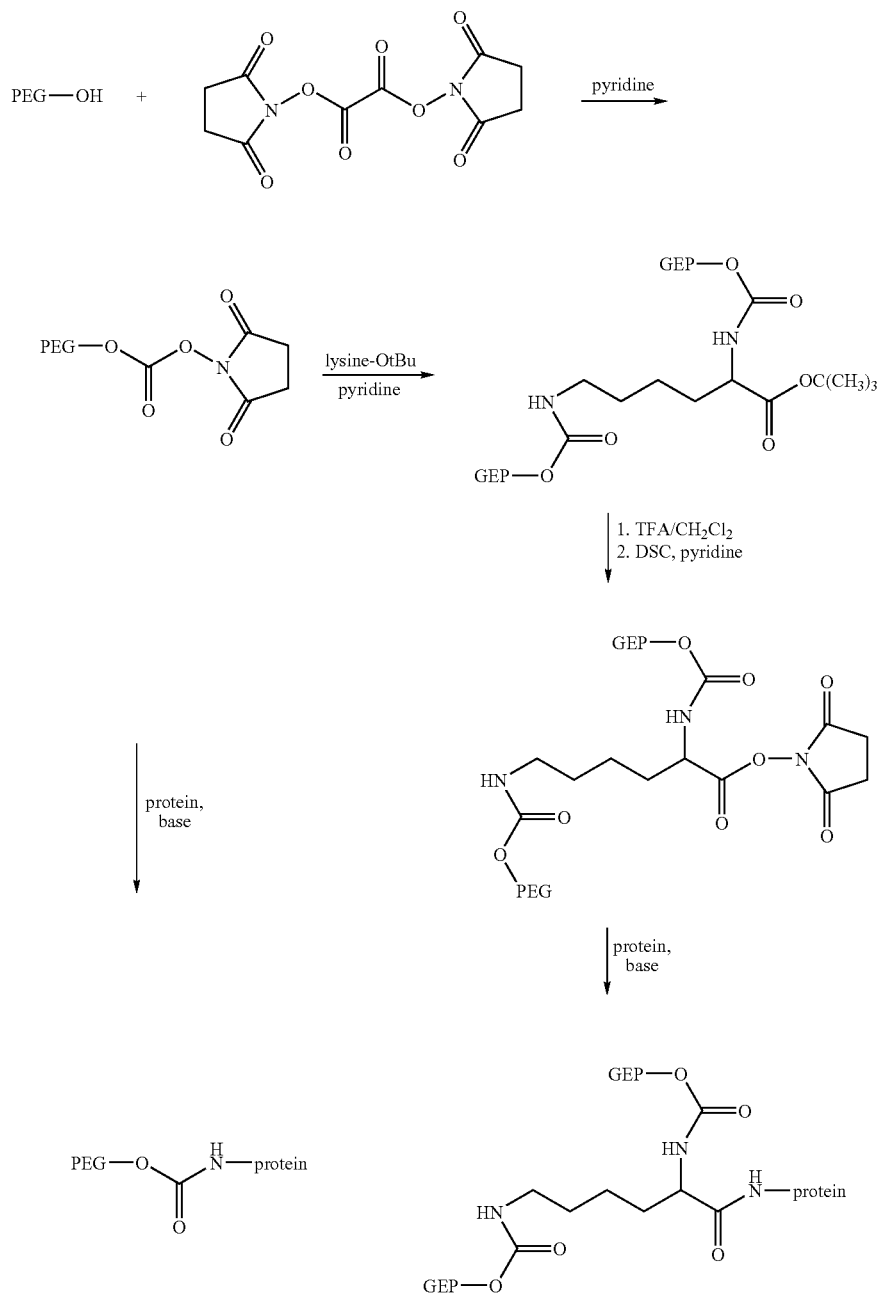
SCHEME VI
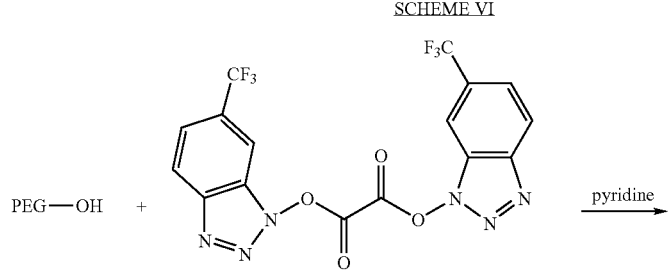

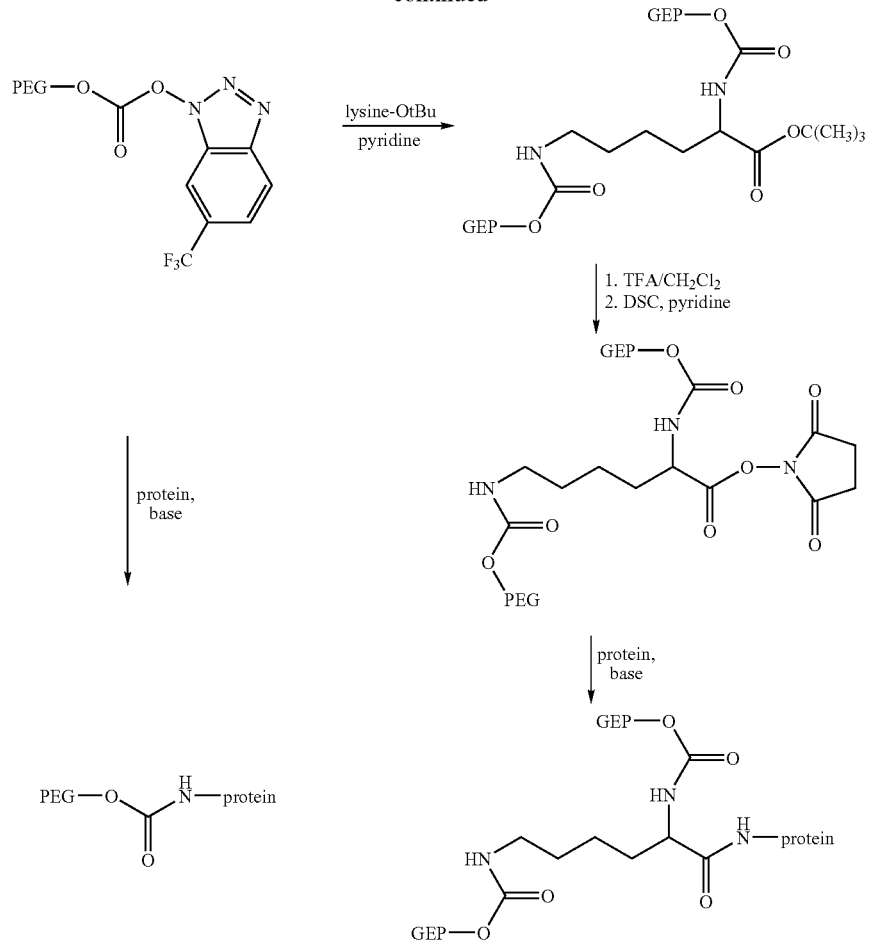
SCHEME VII
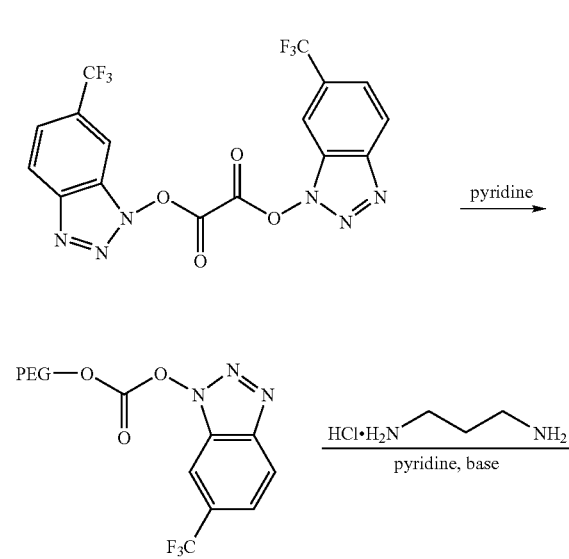
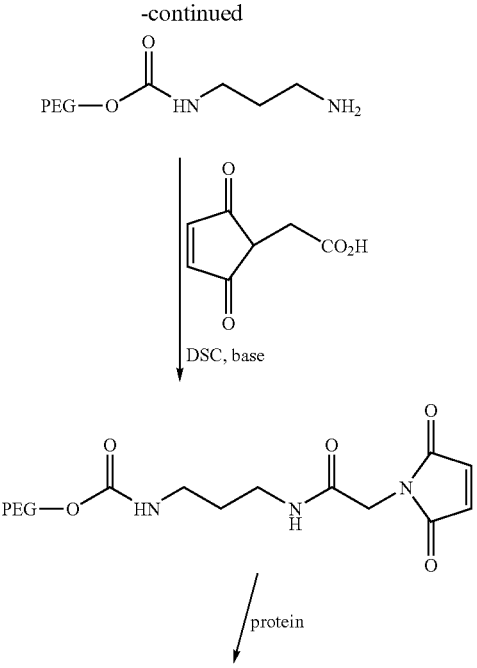

-continued

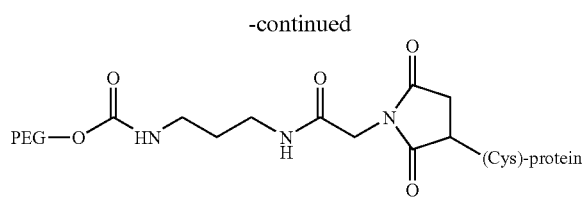

Protein Synthesis and Purification

The peptide and protein to be used in the conjugation are prepared using techniques, which are well established in the art including synthetic techniques (such as recombinant techniques and peptide synthesis or a combination of these techniques) or may be isolated from an endogenous source of the peptide or protein. The peptide synthesis used includes both the solid phase peptide synthesis and the classical solution peptide synthesis techniques. In certain embodiments of the invention, the protein of choice is an antibody. Techniques for the production of antibodies are following:

Polyclonal Antibodies: polyclonal antibodies are generally produced in animals by multiple subcutaneous (sc) or intrperitoneal (ip) injections of the relevant antigen and an adjuvant. It may be useful to conjugate the relevant antigen to a carrier protein that is immunogenic in the species to be immunized, e.g., keyhole limpet hemocyanin, bovine thyroglobulin, serum albumin, or soybean trypsin inhibitor using a bifunctional linkers such as maleimidobenzoyl sulfosuccinimide ester, glutaraldehyde, or succinic anhydride.

Monoclonal antibodies: monoclonal antibodies are obtained from a population of substantially homogeneous antibodies, i.e., the individual antibodies comprising the population are identical except for possible naturally occurring mutations that may be present in minor amounts. For example, monoclonal antibodies may be prepared using the hybridoma technique first described by Koehler et al. in Nature 256, 495 (1975), or may be made by recombinant DNA methods (U.S. Pat. No. 4,816,567).

In the hybridoma method, a mouse or other appropriate animals, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principle and Practice, pp. 59–103 (Academic Press, 1986).

The hybridoma cells thus prepared are seeded and grown in a suitable culture medium that preferably contains one or more substances that inhibit the growth or survival of the unfused, parental myeloma cells. Culture medium in which hybridoma cells are growing is assayed for production of monoclonal antibodies directed against the antigen. After hybridoma cells that produce antibodies of the desired specificity, affinity, and/or activity are identified, the clones may be subcloned by limiting dilution procedures and grown by standard methods (Goding, Monoclonal Antibodies: Principle and Practice, pp. 59–103 (Academic Press, 1986). The monoclonal antibodies secreted by the subclones are suitably separated from the culture medium, ascites fluid, or serum by conventional immunoglobulin purification techniques such as, for example, protein A-Sepharose, hydroxylapatite chromatography, gel electrophoresis, dialysis, or affinity chromatography.

Humanized and human antibodies: methods for humanizing non-human antibodies are well known in the art. Generally, a humanized antibody has one or more amino acid residues introduced into it from a source, which is non-human. These non-human amino acid residues are often referred to as "import" residues, which are typically taken from an "import" variable domain. Humanization can be essentially performed following the method of Winter and co-workers [Jones et al., Nature, 321, 522–525 (1986); Riechmann et al., Nature, 332, 323–327 (1988); Verhoeyen et al., Science, 239, 1534–1536 (1988)] by substituting rodent CDRs or CDR sequences for the corresponding sequence of a human antibody. Accordingly, such "humanized" antibodies are chimeric antibodies (U.S. Pat. No. 4,816,567), wherein substantially less than an intact human variable domain has been substituted by the corresponding sequence from a non-human species.

Alternatively, it is now possible to produce transgenic animals (e.g. mice) that are capable, upon immunization, of producing a full repertoire of human antibodies in the absence of endogenous immunoglobulin production. See e.g., Jakobovits et al., Proc. Natl. Acad. Sci. USA, 90, 2551 (1993); Jakobovits et al., Nature, 362, 255–258 (1993); Brueggermann et al., Year in Immmuno., 7, 33 (1993). Human antibodies can also be obtained from phage-display libraries [Hoogeboom et al., J. Mol. Biol., 227, 381 (1991); Marks et al., J. Mol. Biol., 222, 581–597 (1991)].

Formulation

After preparation of the peptide or protein of interest as described above, a pre-lyophilized formulation is prepared. The amount of protein present in the pre-lyophilized formulation is determined by taking into account the desired final dose volumes, mode(s) of administration etc. The protein is generally present in solution.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulation may also be suitable. Where, the lyoprotectant is a sugar and the protein is an antibody, exemplary lyoprotectant concentrations in the pre-lyophilized formulation are from about 5 mM to about 500 mM, and preferably from about 20 mM to about 300 mM, and most preferably from about 40 mM to about 100 mM.

The ratio of the protein to lyoprotectant is selected for each protein and lyoprotectant combination. In the case of an antibody as the protein of choice and a sugar as the lyoprotectant for generating an isotonic reconstituted formulation with a high protein concentration, the molar ratio of lyoprotectant to antibody may be from about 50 to about 1500 moles to 1 mole antibody, and preferably from about 200 to about 1000 moles of lyoprotectant to 1 mole of antibody.

In another embodiment of the present invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates, triton, poloxamers, sodium dodecyl sulfate, sodium laurel sulfate, polyethylene glycol, polypropylene glycol, etc. The amount of surfactant added is such that it reduces aggregation of the reconstituted protein and minimizes the formation of particulates after reconstitution.

In another embodiment of the present invention, a mixture of the lyoprotectant (e.g. glucose, fructose, sucrose, maltose, or trehalose) and a bulking agent (e.g. mannitol or glycine) is used in the preparation of the pre-lyophilized formulation.

Other pharmaceutically acceptable carriers, excipients or stabilizers such as those described in Remington's Pharmaceutical Sciences 16$^{th}$ edition, Osol, A. Ed. (1980) may be included in the pre-lyophilized formulation provided that they do not adversely affect the desired characteristics of the formulation.

The formulation herein may also contain more than one protein as necessary for the particular indication being treated, preferably those with complementary activities that do not adversely affect the other protein. The formulation to be used for in vivo administration must be sterile. This is readily achieved by filtration through a sterile membrane, prior to, or following, lyophilization and reconstitution. Alternatively, sterility of the entire mixture may be accomplished by autoclaving the ingredients, except for protein, at about 120° C. for about 30 minutes.

After the protein, lyoprotectant and other optional components are mixed together, the formulation is lyophilized. Many different freeze-dryers are available for this purpose. In general, the protein formulation is lyophilized in bulk. In some instances, it may be desirable to lyophilize the protein formulation in the container in which reconstitution of the protein is to be carried out in order to avoid transfer step.

Reconstitution of the Lyophilized Formulation

At the desired stage, typically, when it is time to administer the protein to the patient, the lyophilized formulation may be reconstituted with a diluent such that the protein concentration in the reconstituted formulation is at least 30 mg/ml, for example from about 30 mg/ml to about 500 mg/ml.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection, a pH buffered solution, sterile saline solution, Ringer's solution or dextrose solution. The diluent optionally contains a preservative such as benzyl alcohol or phenol. The amount of the preservative employed is determined by assessing different preservative concentration for compatibility with the protein and preservative efficacy testing.

Administration of the Reconstituted Formulation

The reconstituted formulation is administrated to a mammal in need of treatment with the peptide or the protein, preferably a human, in accord with known methods, such as intravenous administration as a bolus or by continuous infusion over a period of time, by intraperitoneal, intramuscular, intracerobrospinal, subcutaneous, intraarticular, intrasynovial, intrathecal, oral topical, or inhalation routes.

In one embodiment, the reconstituted formulation is administered to the mammal by subcutaneous administration. For such purposes, the formulation may be injected using a syringe. However, other devices for the administration of the formulation area available such as injection devises, injection pens, needle less devices, and subcutaneous patch delivery systems.

The appropriate dosage of the protein will depend, for example, on the condition to be treated, the severity and course of the condition, whether the protein is administered for preventive or therapeutic purposes, previous therapy, the patient' clinical history and response to the protein, the type of the protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question. Where the protein of choice is an antibody, from about 0.1–25 mg/kg is a preferred initial dosage for administration to the patient, whether, for example, by one or more separate administrations. However, other dosages may be useful. The progress of this therapy can be easily monitored by conventional techniques.

The following is a list of definitions of various terms used herein:

As used herein, the term "PEG" refers to any of several condensation polymers of ethylene glycol having the general formula represented by the structure

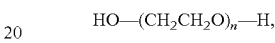

wherein n can be from about 5 to about 1100. PEG has an average molecular weight between 300 and 60,000 Daltons. Preferably, the PEG used in the present invention has an average molecular weight between. 2,000 and 40,000 Daltons. More preferably, between 5,000 and 20,000 Daltons.

"PEG" is also known as polyoxyethylene, polyglycol, and polyether glycol. The polymer can be homopolymer or block co-polymer, straight chain or branched, unsubstituted or substituted, preferably with lower alkyl, lower hydroxy alkyl, and lower alkoxy group.

"PEG" is also meant to include water-soluble polyoxyethylated polyols such as polyoxyethylated sorbitol, polyoxyethylated glucose, polyoxyethylated glycerol, etc.

As used herein, the term "mPEG" refers to a PEG, which is capped at one end with a methyl group. The mPEG can be represented structurally as

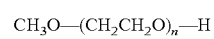

As used herein, the term "linker" refers to molecular fragment that links the PEG to a biologically active nucleophile. The fragment typically has two functional groups that can be coupled to or activated to react with another linker or directly with the biologically active nucleophile. As an example, ω-aminoalkanoic acid such as lysine is commonly used. In the present invention, multiple linkers are also used to link the PEG with the target peptides or proteins i.e.

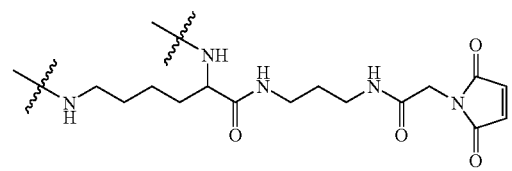

As used herein, the term "aminoalkanoic acid" refers to carboxylic acid with one or more amino groups in the backbone of the molecule. The amino group can be at the terminal position or located internally or both, such as lysine.

As used herein, the term "biologically active nucleophile" refers to a compound containing at least one nucleophilic moiety, more specifically, to biologically active peptides and proteins.

As used herein, the term "peptide" refers to a short molecule of short chain of about 2 to about 50 natural amino acids. The amino acid may also include unnatural amino acids such as β-amino acids or D-amino acids.

As used herein, the term "protein" refers to a long chain of amino acid based polymer (polypeptide), which is sufficient to produce the higher levels of tertiary and or quaternary structure. Proteins may be composed of single or multi polypeptide chains, linear or cyclic, and may further be substituted such as phosphorylated or glycosylated. The size of the proteins covers a rather wide range from about 50 to over 1000 amino acids.

Examples of peptides and proteins encompassed within the definition herein include mammalian peptides and proteins, such as, e.g. insulin, glucagon, vasopressin, calcitonin, vasoactive intestinal peptide (VIP), α-melanocyte-stimulating hormone (α-MSH), secretin, cholecystokinin (CCK), endothelin, somatostatin, substance P, parathyroid hormone (PTH), oxytocin, dynorphin, adrenocorticotropic hormone (ACTH), antibodies, growth hormone (GH), including human and bovine growth hormone, growth hormone receptor antagonist, growth hormone releasing factor (GRF), epidermal growth factor (EGF), transforming growth factor (TGF) α and β, insulin-like growth factor (IGF) I and II, interleukins, interferon α, β, and γ, tumor necrosis factor (TNF) α and β, platelet-derived growth factor, granulocyte colony stimulating factor, granulocyte macrophage colony stimulating factor, erythropoeitin, thrombopoeitin, FLT-3, superoxide dismutase (SOD), immunotoxins, regulatory proteins, transport proteins, and biologically active fragments or variants of any of the above listed polypeptides.

As used herein, the term "antibody" is used in the broadest sense and refers to polyclonal antibodies, monoclonal antibodies, humanized antibodies, and fragments thereof such as $F_{ab}$, $F_{(ab)2}$, $F_v$, and any fragment that has the antigen binding function or the parent antibody.

As used herein, the term "monoclonal antibody" refers to an antibody composition having a homogeneous antibody population. The term encompasses whole immunoglobulins as well as fragments such as $F_{ab}$, $F_{(ab)2}$, $F_v$, and any fragment that has the antigen binding function or the parent antibody. Furthermore, the term also includes "chimeric" antibodies in which a portion of the heavy chain and/or light chain is identical with or homologous to corresponding sequences in antibodies derived from a particular species or belonging to a particular class or subclass, while the remainder of the chain(s) is identical with or homologous to corresponding sequences in antibodies derived from another species or belonging to another class or subclass, as well as fragments of such antibodies, so long as they exhibit the desired biological activity.

As used herein, the term "humanized antibody" refers to that at least a portion of the framework regions of an immunoglobulin are derived from human immunoglobulin sequences.

As used herein, the term "PEGylation" or "PEGylated" peptides/proteins refers to a process of attaching covalently one or more PEG molecules to a peptide or protein to form PEGylated peptide/protein.

All patents and references are incorporated by reference in their entirety as if written herein.

The present invention provides methods for preparing PEG active carbonate esters using N,N'-disuccinimidyl oxalate or 1,1'-bis[6-(trifluoromethy)-benzotriazolyl] oxalate. The resulting PEG active esters are useful in the preparation of PEG-peptide or PEG-protein conjugates. N,N'-disuccinimidyl oxalate is commercially available and 1,1'-bis[6-(trifluoromethy)benzotriazolyl]-oxalate can be prepared according to published procedures.

The general synthetic sequences described in SCHEME I–VII are intended to be merely illustrative of the present invention, and not limiting thereof in either scope or spirit. Those with skill in the art will readily understand that known variations of the conditions and processes described in the SCHEMES and EXAMPLES can be used in the present invention.

EXAMPLES

Example 1

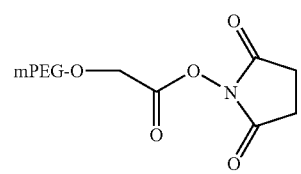

N,N'-disuccinimidyl oxalate (5.7 g, 20 mmoles) ) and monomethyl polyethylene glycol (mPEG, M.W. 6,000; 6 g, 1 mmol) are stirred in dichloromethane (50 ml) at room temperature in the presence of pyridine (2 ml) overnight. The solid is filtered and the filtrate is treated with ether (600 ml). The white precipitates are filtered and washed thoroughly with ether. The precipitate is redissolved in dichloromethane (40 ml) and treated with ether (500 ml). The process is repeated once to give the title compound as a white solid material (5.85 g).

Example 2

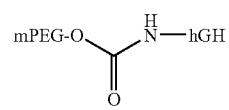

A human Growth Hormone (hGH) solution is prepared at a concentration of 2 mg/ml in 0.2 M borate buffer of pH 8.5. The title compound of Example 1 is added in small portion to the protein solution in a molar ratio of approximately 5:1 mPEG active ester per protein. The reaction mixture is stirred for about 2 to 3 hours. The mPEG-hGH conjugate is purified by ultrafiltration and concentrated in a Amicon system with a PM 10 membrane (cut off 10,000) to remove N-hydroxysuccinimide produced by the reaction. The conjugate is further purified from the excess of unreacted mPEG by gel filtration chromatography on a Pharmacia Superose 12 column. The filtrate is lyophilized to give a white solid product.

Example 3

1-hydroxy-6-(trifluoromethyl)benzotriazole

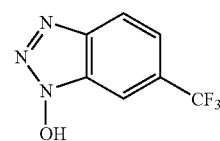

The title compound is prepared according to the procedure described by K. Takeda [J. Org. Chem., 50, 273, (1985)]. A mixture of 4-chloro-3-nitro-α,α,α-trifluorotoluene (50.0 g, 0.22 moles) and hydrazine hydrate (33.0, 0.33 moles) in absolute ethanol (75 ml) is refluxed for 24 h. After removal of the solvent under reduced pressure, the residue is dissolved in 10% aqueous sodium carbonate solution. The solution is washed with ether to remove the starting material and acidified with concentrated HCl to precipitate the product, which is washed with water and dried to obtain 40.0 g of the title compound. This product is recrystallized from ether.

Example 4

1,1'-bis[6-(trifluoromethyl)benzotriazolyl]oxalate (BTBO)

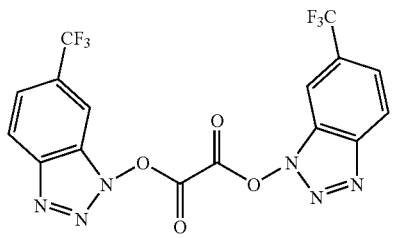

The title compound is prepared according to the procedure described by K. Takeda [J. Org. Chem., 50, 273, (1985)]. A solution of EXAMPLE 3 (40.6 g, 0.2 moles) in dry ether (600 ml) is vigorously stirred with a mechanical overhead stirrer, whereupon oxalyl chloride (50.0 g, 0.4 moles) is slowly added at room temperature. After stirring for 3 hours, a white precipitate is filtered and washed with dry ether and a trace of dry acetone. Pure crystal of the title compound (35.0 g) is obtained without further recrystallization.

Example 5

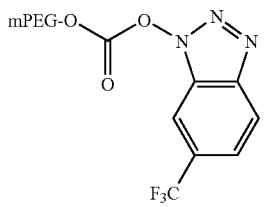

1,1'-bis[6-(trifluoromethyl)benzotriazolyl]oxalate (9.2 g, 20 mmoles) ) and monomethyl polyethylene glycol (mPEG, M.W. 6,000; 6.0 g, 1.0 mmol) are stirred in dichloromethane (70 ml) at room temperature in the presence of pyridine (5 ml) overnight. The solid is filtered and the filtrate is treated with 700 ml of ether. The white precipitates are filtered and washed thoroughly with dry ether. The precipitate is redissolved in dichloromethane (60 ml) and treated with ether (600 ml). The process is repeated twice to give the title compound as a white solid material (5.9 g).

Example 6

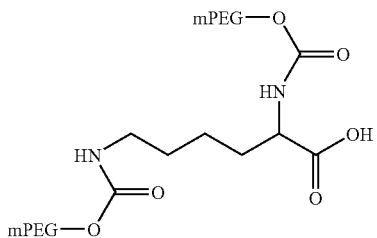

The title compound of Example 5 (5.9 g, 1.0 mmol), lysine t-butyl ester. HCl (0.53 g, 2.0 mmoles), and diisopropylethylamine (0.26 g, 2 mmoles) are stirred in DMF/pyridine (1:1; 50 ml) at room temperature overnight. Ether (600 ml) is added to the reaction mixture and the precipitate is filtered. The precipitate is dried in vacuum dessicator and treated with trifluoroacetic acid in dichloromethane (200 ml) for 30 minutes. Ether (500 ml) is added to the solution and the precipitate is filtered. The solid is redissolved in dichloromethane (75 ml) and ether (500 ml) is added. The precipitate is filtered and washed thoroughly with ether. The dried precipitate is used without any further purification.

Example 7

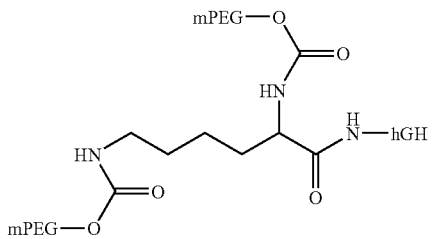

The title compound of Example 6 (3 g) and N,N'-disuccinimidyl carbonate (DSC; 2.5 g, 10 mmoles) are dissolved in DMF (30 ml). After addition of pyridine (5 ml), the reaction mixture is stirred at room temperature overnight. The solid is filtered and the filtrate is treated with ether (400 ml). The white precipitates are filtered and washed thoroughly with dry ether. The precipitate is redissolved in dichloromethane (40 ml) and treated with ether (400 ml). The process is repeated twice to give the title compound as a white solid material (2.9 g). Separately, a human Growth Hormone (hGH) solution is prepared at a concentration of 2 mg/ml in 0.2 M borate buffer of pH 8.5. The DSC activated Example 6 is then added in small portion to the protein solution in a molar ratio of approximately 5:1 mPEG active ester per protein. The reaction mixture is stirred for about 2 to 3 hours. The mPEG-hGH conjugate is purified by ultrafiltration and concentrated in an Amicon system with a PM 10 membrane (cut off 10,000) to remove N-hydroxysuccinimide produced by the reaction. The conjugate is further purified from the excess of unreacted mPEG by gel filtration chromatography on a Pharmacia Superose 12 column. The filtrate is lyophilized and the product is placed in the cold room.

Example 8

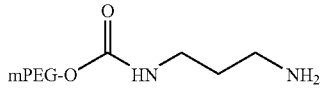

The title compound of Example 5 ((5.9 g, 1.0 mmol),), 1,3-diaminopropane (0.74 g, 10 mmoles) are stirred in pyridine (50 ml) under nitrogen overnight. Ether (500 ml) is added to the reaction mixture and the precipitate is filtered. The solid is redissolved in dichloromethane (50 ml) and ether (500 ml) is added. The solid is collected by filtration and dried in vacuum to give 5.8 g of white material.

Example 9

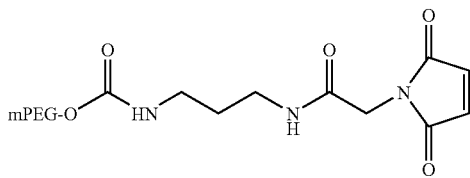

The title compound of Example 8 (5.8 g, 0.095 mmoles) is added to a mixture of N-(2-carboxyethyl)maleimide (0.31 g, 2.0 mmoles) and N,N'-disuccinimidylcarbonate (0.52 g, 2 mmoles) in DMF/pyridine (1:1; 50 ml). The reaction mixture is stirred at room temperature overnight. Ether (600 ml) is added to the mixture and the precipitate is then filtered. The process is repeated once and the solid is filtered. The product is dried in vacuum and used without any further purification.

Example 10

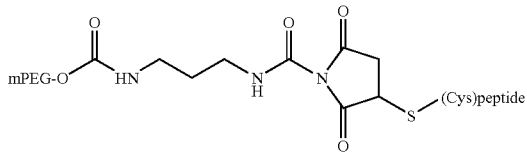

The title compound of Example 9 (5.7 g, 0.9 mmoles) and reduced CDP 870 Fab' (0.6 mmoles) are stirred in sodium acetate, pH 4.5 (20 mM, 60 ml) at room temperature for 2 hours. The reaction mixture is allowed to stand overnight and dialyzed against sodium acetate (50 mM) and NaCl (125 mM), pH 5.5 using a 10 Kda membrane. The final product is stored at −70° C.

What is claimed is:

1. A method of producing an activated ester of polyethylene glycol (PEG), comprising the step of activating PEG with N,N'-disuccinimidyl oxalate or 1,1'-bis[6-(trifluoromethyl)benzotriazolyl] oxalate under the appropriate conditions.

2. The method according to claim 1, comprising the step of activating PEG with N,N'-disuccinimidyl oxalate.

3. The method according to claim 2, wherein the ratio of N,N'-disuccinimidyl oxalate to PEG is 30:1 or less.

4. The method of producing a N,N'-disuccinimidyl ester of polyethylene glycol (PEG) according to claim 2, wherein an organic base is used as a catalyst.

5. The method of producing a N,N'-disuccinimidyl ester of polyethylene glycol (PEG) according to claim 4, wherein the base catalyst is selected from the group consisting of pyridine and N,N'-4-dimethylaminopyridine.

6. A method of conjugating an activated ester of polyethylene glycol (PEG) and a biologically active nucleophile, comprising the steps:
   (a) activating PEG with N,N'-disuccinimidyl oxalate;
   (b) providing the biologically active nucleophile; and
   (c) reacting the PEG active ester and the biologically active nucleophile under appropriate conditions.

7. A method of conjugating a PEG-linker and a biologically active nucleophile, comprising the steps:
   (a) activating PEG with N,N'-disuccinimidyl oxalate;
   (b) providing a linker;
   (c) reacting the PEG active ester with the linker; and
   (d) reacting the resulting PEG-linker with a biologically active nucleophile under appropriate conditions.

8. The method according to claim 6 or 7 wherein said biologically active nucleophile is a peptide or a protein.

9. The method according to claim 8, wherein said PEG active ester is reacted with said peptide or protein in the molar ratio of between 1 and 30 moles active ester to 1 mol peptide or protein or with said linker in the molar ratio of 1 mole active ester to 1 to 10 moles linker.

10. The method according to claim 7, wherein the PEG-linker(s) conjugate is activated with N,N'-disuccinimidyl oxalate, and subsequently reacted with a peptide or protein in the molar ratio of between 1 and 30 moles active ester to 1 mol peptide or protein to form PEG-linker(s) peptide or protein conjugate.

11. The method according to claim 1, comprising the step of activating PEG with 1,1'-bis[6-(trifluoromethyl)benzotriazolyl] oxalate.

12. The method according to claim 11, wherein the ratio of 1,1'-bis[6-(trifluoromethyl)benzotriazolyl] oxalate to PEG is 30:1 or less.

13. The method of producing a 1,1'-bis[6-(trifluoromethyl)benzotriazolyl] ester of polyethylene glycol (PEG) according to claim 11, wherein an organic base is used as a catalyst.

14. The method of producing a 1,1'-bis[6-(trifluoromethyl)benzotriazolyl] ester of polyethylene glycol (PEG) according to claim 13, wherein said base catalyst is selected from the group consisting of pyridine and N,N'-4-dimethylaminopyridine.

15. A method of conjugating an activated ester of polyethylene glycol (PEG) and a biologically active nucleophile, comprising the steps:
   (a) activating PEG with 1,1'-bis[6-(trifluoromethyl)benzotriazolyl] oxalate;
   (b) providing the biologically active nucleophile; and
   (c) reacting the PEG active ester and the biologically active nucleophile under appropriate conditions.

16. A method of conjugating a PEG-linker and a biologically active nucleophile, comprising the steps:
   (a) activating PEG with 1,1'-bis[6-(trifluoromethyl)benzotriazolyl] oxalate;
   (b) providing a linker;
   (c) reacting the PEG active ester with the linker; and
   (d) reacting the resulting PEG-linker with a biologically active nucleophile under appropriate conditions.

17. The method according to claim 15 or 16 wherein said biologically active nucleophile is a peptide or a protein.

18. The method according to claim 17, wherein said PEG active ester is reacted with said peptide or protein in the molar ratio of between 1 and 30 moles active ester to 1 mol peptide or protein or with said linker in the molar ratio of 1 mole active ester to 1 to 10 moles linker.

19. The method according to claim 16, wherein the PEG-linker(s) conjugate is activated with 1,1'-bis[6-(trifluoromethyl)benzotriazolyl] oxalate, and subsequently reacted with a peptide or protein in the molar ratio of between 1 and 30 moles active ester to 1 mol peptide or protein to form PEG-linker(s) peptide or protein conjugate.

* * * * *